United States Patent
Koelper et al.

(10) Patent No.: US 10,071,234 B2
(45) Date of Patent: Sep. 11, 2018

(54) DUAL MATERIAL Y-CONNECTOR

(71) Applicant: Avent, Inc., Alpharetta, GA (US)

(72) Inventors: Crystal E. Koelper, North Barrington, IL (US); Jeffrey S. Nordquist, Lake Barrington, IL (US); Michael C. Shaughnessy, Terrace Park, OH (US); John L. Morici, Wauconda, IL (US)

(73) Assignee: Avent, Inc., Alpharetta, GA (US)

( * ) Notice: Subject to any disclaimer, the term of this patent is extended or adjusted under 35 U.S.C. 154(b) by 10 days.

(21) Appl. No.: 14/553,337

(22) Filed: Nov. 25, 2014

(65) Prior Publication Data
US 2016/0143815 A1    May 26, 2016

(51) Int. Cl.
*A61M 39/10* (2006.01)
*A61J 15/00* (2006.01)
*A61M 39/20* (2006.01)
*A61M 39/08* (2006.01)

(52) U.S. Cl.
CPC .......... *A61M 39/10* (2013.01); *A61J 15/0026* (2013.01); *A61M 39/08* (2013.01); *A61M 39/105* (2013.01); *A61M 39/1011* (2013.01); *A61M 39/20* (2013.01); *A61M 2039/085* (2013.01)

(58) Field of Classification Search
CPC .......... A61M 16/0833; A61M 16/0816; A61M 39/10; A61M 2039/1027; A61M 2025/1045; A61M 39/20; A61M 39/105; A61M 2039/0235; A61M 2039/0261; A61M 2039/0264; A61M 2039/0282; A61M 2039/0288; A61M 2039/0054
See application file for complete search history.

(56) References Cited

U.S. PATENT DOCUMENTS

| 1,755,899 | A | * | 4/1930 | Root | F16L 41/02 |
| | | | | | 285/131.1 |
| 4,668,225 | A | * | 5/1987 | Russo | A61J 15/0015 |
| | | | | | 604/104 |
| 5,082,025 | A | | 1/1992 | DeVries et al. | |

(Continued)

FOREIGN PATENT DOCUMENTS

DE    102009048584    4/2012

OTHER PUBLICATIONS

International Search Report and Written Opinion dated Jan. 29, 2016 for corresponding International Appln. No. PCT/US2015/061751 (12 pages).

*Primary Examiner* — Nathan R Price
*Assistant Examiner* — Melissa A Snyder
(74) *Attorney, Agent, or Firm* — Dority & Manning, P.A.

(57) ABSTRACT

A dual material Y-connector for use in connection with medical tubing systems and the like includes an inner core made of a first material such as a rigid plastic material and an over-layer made of a second material such as a pliable thermoplastic elastomer. The Y-connector comprises a primary arm, a secondary arm and a convergence arm all in fluid communication with one another and may include a tubing segment bonded to the Y-connector convergence arm. The first material can be a transparent copolyester and the second material can be a translucent thermoplastic elastomer. Threaded caps having a multi-indentation configuration can be tethered to one or more arms and be configured to seal one or more Y-connector ports.

19 Claims, 6 Drawing Sheets

(56) References Cited

U.S. PATENT DOCUMENTS

| | | | | |
|---|---|---|---|---|
| 5,234,417 | A | * | 8/1993 | Parks .................. A61J 15/0026 16/2.1 |
| 5,322,073 | A | | 6/1994 | Michels et al. |
| 5,413,561 | A | * | 5/1995 | Fischell ............ A61M 39/0606 604/167.01 |
| 6,375,231 | B1 | | 4/2002 | Picha et al. |
| 6,464,686 | B1 | * | 10/2002 | O'Hara .............. A61B 17/3415 604/256 |
| 8,968,271 | B2 | * | 3/2015 | Guala .................. A61M 39/10 604/533 |
| 2006/0004345 | A1 | * | 1/2006 | McMichael ........... A61M 39/10 604/523 |
| 2006/0027270 | A1 | * | 2/2006 | Truitt .................... A61M 39/02 137/843 |
| 2006/0079850 | A1 | | 4/2006 | Adams et al. |
| 2006/0195066 | A1 | | 8/2006 | Cross, Jr. |
| 2010/0292673 | A1 | * | 11/2010 | Korogi ................ A61M 39/165 604/533 |
| 2011/0065319 | A1 | * | 3/2011 | Oster ................ H01R 13/2414 439/586 |
| 2011/0230828 | A1 | | 9/2011 | Shaughnessy et al. |
| 2012/0041425 | A1 | * | 2/2012 | Tsunematsu .......... A61M 39/10 604/535 |

* cited by examiner

DUAL MATERIAL Y-CONNECTOR

BACKGROUND

Technical Field

This invention relates generally to apparatus, systems, methods, techniques, etc. relating to components in medical tubing systems and/or medical small bore tubing systems, and in particular for components used in systems used for feeding and medicating patients using tubular delivery.

Description of Related Art

Various medical systems utilize components that are intended to deliver one or more fluids to a patient or other person being treated. One example of such a system is an enteral feeding system in which fluid nutrient formula or the like is delivered via a series of tubing segments to a patient. In such systems it may be desirable to use one or more connectors to introduce a second fluid (e.g., a medication, flushing solution, or additional nutrient formula) into the fluid delivery apparatus. Such connectors can also be utilized in the opposite flow direction, for example, to collect stomach aspirate, reflux, or gasses escaping from the patient's GI tract. One way to do this is by using a Y-connector that has two (or more) input ports, each of which may have an input tubing segment affixed to it, and an output port that delivers any fluids introduced into the Y-connector's input ports. Apparatus, systems, methods, techniques, etc. that provide improved fabrication, assembly, use and operation of Y-connectors would represent a significant advancement in the art.

SUMMARY

Embodiments of a Y-connector include a dual material Y-connector for use in connection with medical tubing systems and the like. A dual material Y-connector includes an inner core made of a first material such as a rigid plastic material and an over-layer made of a second material such as a pliable thermoplastic elastomer. The Y-connector comprises a primary or central arm, one or more secondary arms that branch off of the primary arm at an angle, and a convergence arm at which the primary arm and any secondary arms meet, all in fluid communication with one another. A tubing segment is bonded to the Y-connector convergence arm in some embodiments. The first material can be a transparent copolyester and the second material can be a translucent thermoplastic elastomer possessing good gripping characteristics. Threaded caps configured to seal one or more Y-connector ports can have ridges and/or other gripping means provided on each cap's periphery. Moreover, each cap's top can be a multi-indentation configuration. The caps are tethered to each arm in some embodiments.

BRIEF DESCRIPTION OF THE DRAWINGS

Embodiments of the present invention will be readily understood by the following detailed description in conjunction with the accompanying drawings, wherein like reference numerals designate like structural elements, and in which.

DETAILED DESCRIPTION

The following detailed description of the invention, including the Figures, will refer to one or more invention embodiments, but is not limited to such embodiments. Rather, the detailed description is intended only to be illustrative. Those skilled in the art will readily appreciate that the detailed description given with respect to the Figures is provided for explanatory purposes as the invention extends beyond such specific embodiments. Embodiments of the invention provide apparatus, systems, methods, techniques, etc. including and pertaining to medical tubing systems and/or medical small bore tubing systems. Specific examples will be used herein to illustrate embodiments that include (but are not limited to) Y-connectors and related apparatus and methods of making such devices. Other structures and uses will be apparent to those skilled in the art after considering the following disclosure and the Figures provided herewith. Some embodiments will be shown and explained in connection with a Y-connector used in an enteral feeding system specifically, though embodiments can be used in connection with other systems, configurations and uses.

A Y-connector typically is characterized by a housing having a primary channel defined by a generally tubular central body member having an "entry" port connected to an "exit" port via the primary channel. Each port typically can be affixed to a tubing segment or the like either removably (e.g., using friction or a mechanical engaging means) or permanently (e.g., using adhesive or solvent bonding). The Y-connector can, in use, assume a wide variety of orientations that do not require one port to be above or below another and further do not require that a given port be used as an "entry" port or an "exit" port (fluids such as liquids, gases, etc. can flow in either direction through any of the ports and the primary and secondary channels); thus such orientations in the Figures, the terminology herein, and/or the description herein are non-limiting and are used only to assist in explaining the relative structure and operation of embodiments of a Y-connector. A secondary "entry" port (e.g., for the administration of entering medication and/or to channel exiting reflux materials during enteral feeding gastric pressure relief) is provided in a secondary, offshoot tubular arm having a secondary channel that intersects the primary channel through the tubular body member. Such Y-connectors can be used in medical tubing systems or medical small bore tubing systems (e.g., enteral feeding, respiratory, epidural, vascular, dialysis treatment, and intrathecal) and in other situations.

Figure 1A:
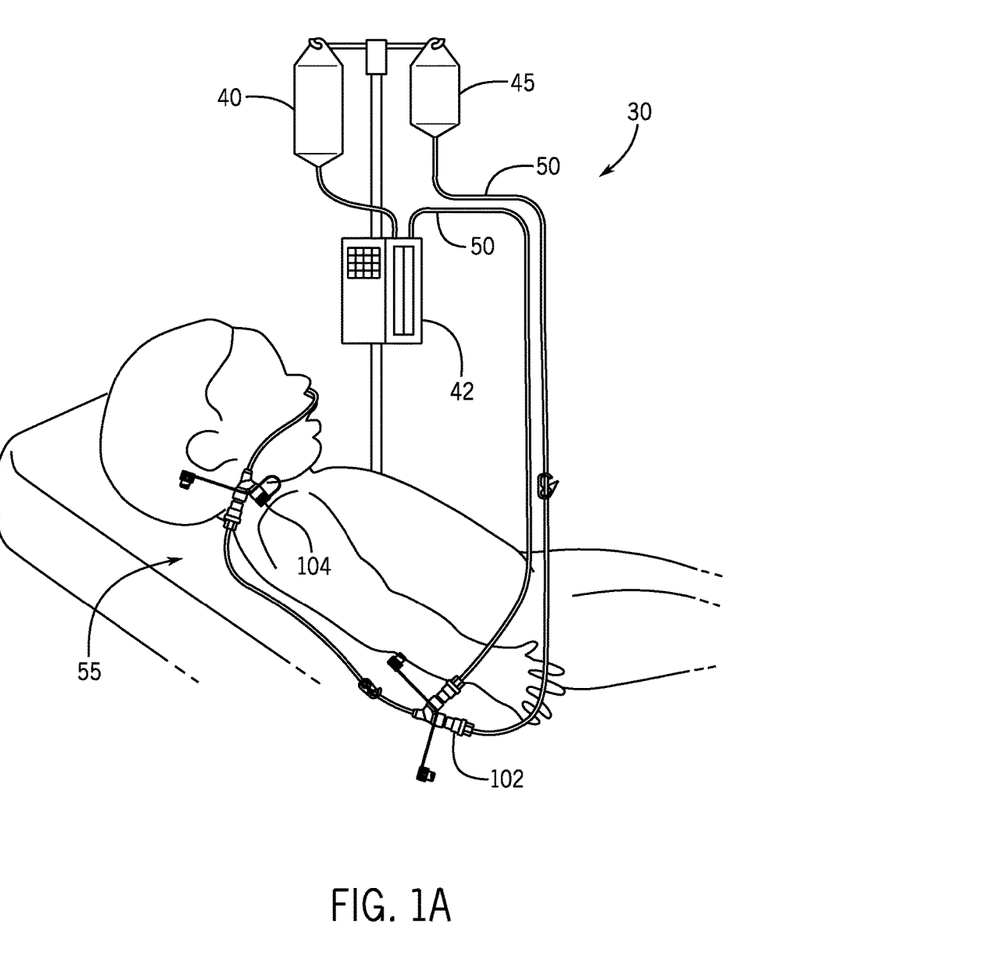
FIG. 1A is a perspective view of a nasogastric/nasointestinal enteral feeding system implementing one or more embodiments of a dual material Y-connector.
Figure 1B:
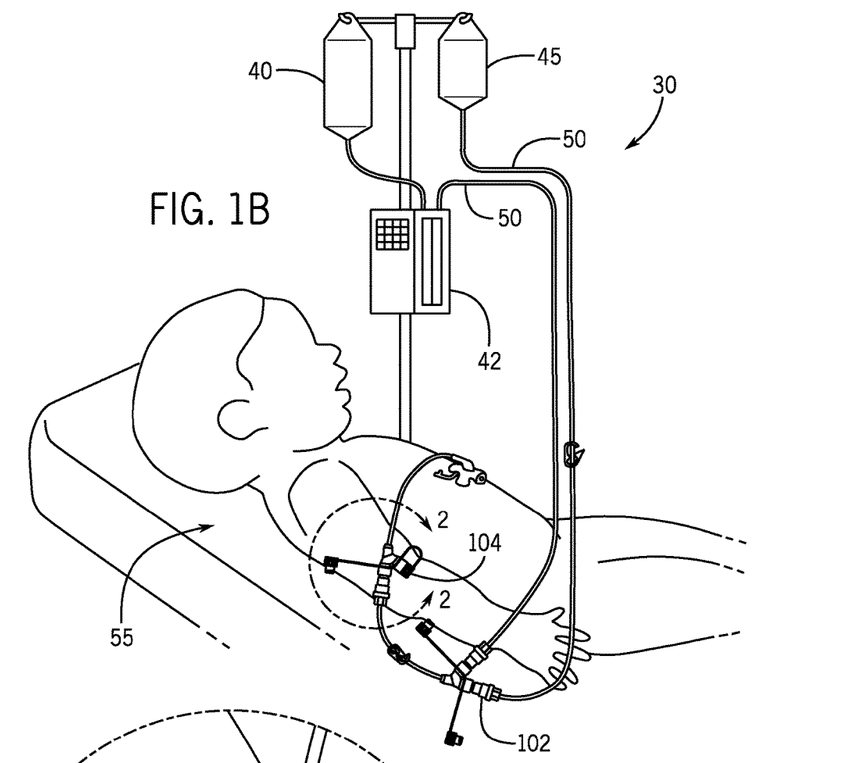
FIG. 1B is a perspective view of a gastrostomy enteral feeding system implementing one or more embodiments of a dual material Y-connector.
Figure 2:
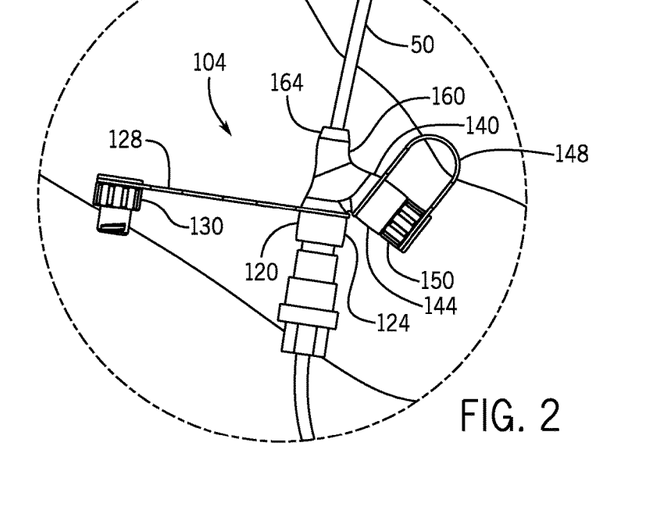
FIG. 2 is a detailed view of a dual material Y-connector defined by the line 2-2 of FIG. 1A.

FIGS. 1A and 1B illustrate one or more embodiments of a dual material Y-connector in an enteral feeding system 30 (a nasogastric/nasointestinal system is shown in FIG. 1A; a gastrostomy system is shown in FIG. 1B). Nutrient formula is provided from a suspended bag 40 and is pumped using pump 42 via tubing 50. Gastric pressure relief may be provided using a reflux material container 45 that likewise is connected using tubing 50. Nutrient formula and reflux material channeling can be accomplished using one embodiment of a Y-connector 102. Moreover, if medication, flushing solution, or the like is to be supplied to the patient 55 in connection with the nutrient formula, then a second Y-connector 104 can be used as well. A detail of the second Y-connector 104 from FIG. 1A is shown in FIG. 2.

Figure 3:
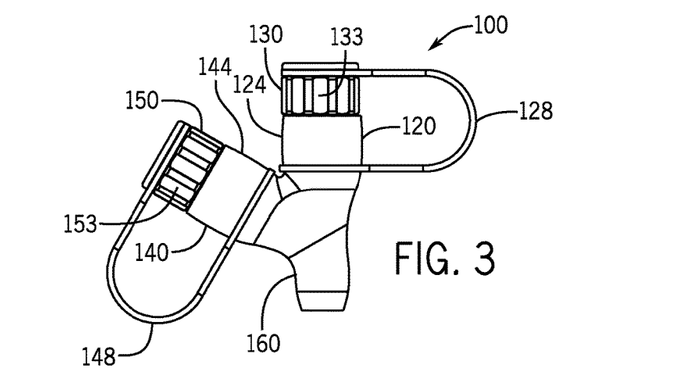
FIG. 3 is a side view of a dual material Y-connector according to one or more embodiments.
Figure 4:
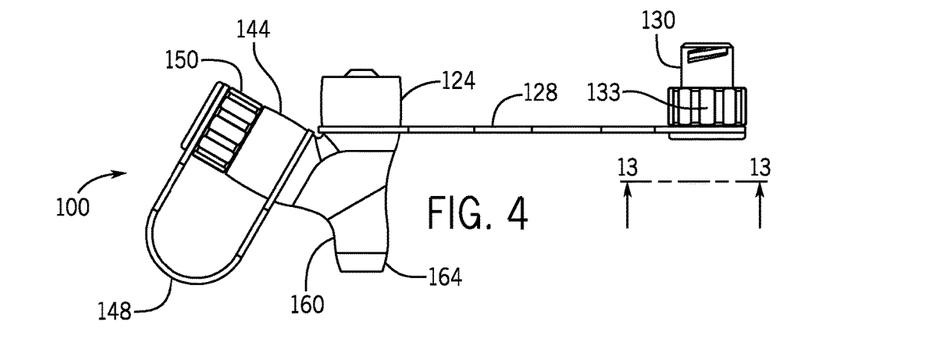
FIG. 4 is a side view of a dual material Y-connector according to one or more embodiments.
Figures 5, 13:
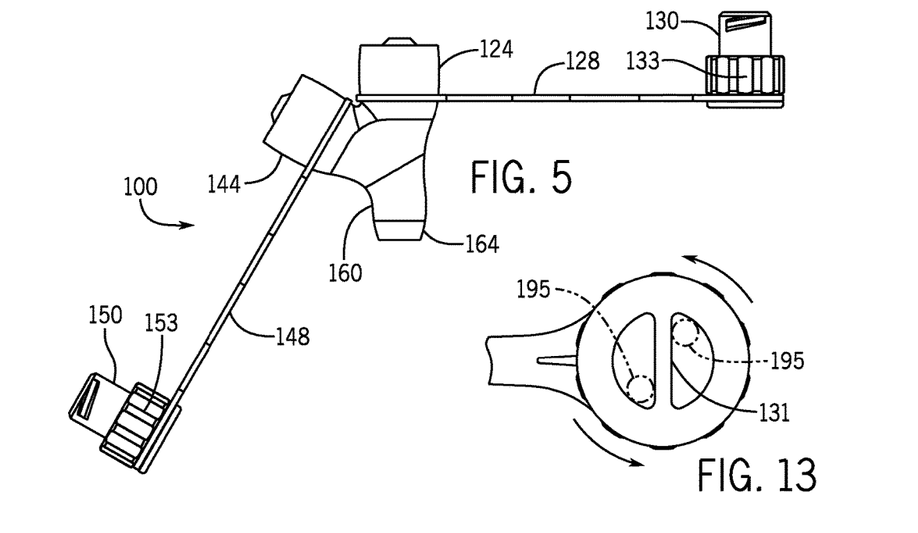
FIG. 5 is a side view of a dual material Y-connector according to one or more embodiments.
FIG. 13 is a top view of a securable Y-connector cap.
Figure 6:
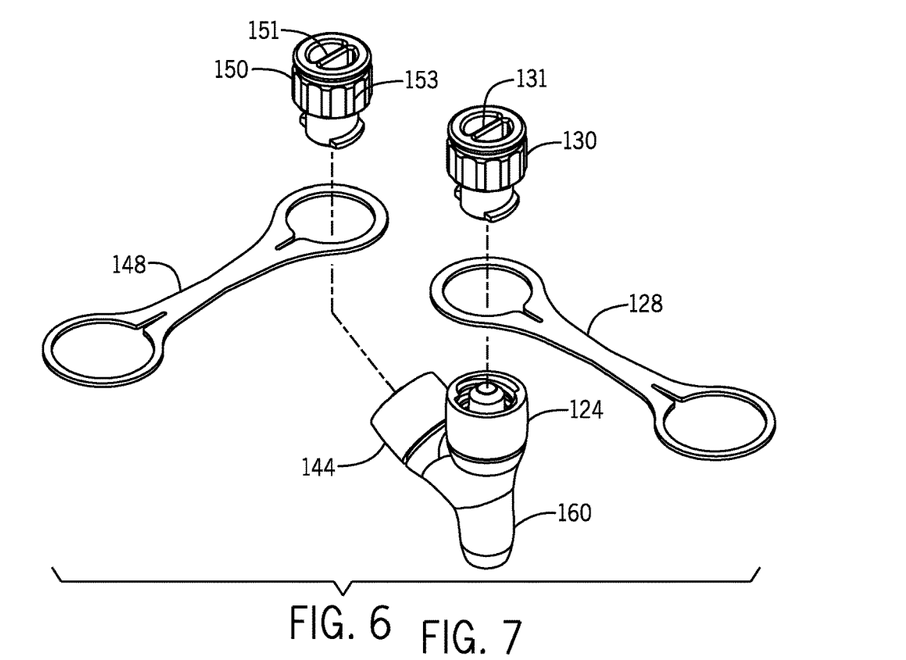
FIG. 6 is an exploded view of a dual material Y-connector according to one or more embodiments.

One or more embodiments of a dual material Y-connector 100 according to the present invention are shown as complete assemblies in FIGS. 3-5. Generally, Y-connector 100 has a primary arm 120 (e.g., a primary "entry" port) and a secondary arm 140 (e.g., a secondary "entry" port), both of which are connected to a convergence arm 160 (e.g., an "exit" port). Convergence arm 160 has a generally cylindrical stem and is the "lower part" of the "Y" shape of Y-connector 100. Some dual material Y-connector embodiments disclosed herein have an inner core unit 110 made substantially or completely of a first material, an exemplary embodiment of which is shown separately in FIG. 11, and an over-layer unit 114 made substantially or completely of a second material, an exemplary embodiment of which is shown separately in FIG. 12.

Core unit 110 defines the various arms, channels and connectors of the Y-connector and in some embodiments is made of a rigid material such as a suitable copolyester or the like. An amorphous copolyester product typically has suitable appearance, clarity and mold release properties (usable with injection molding, for example). It also provides appropriate toughness, hydrolytic stability, heat resistance, and chemical resistance and has been formulated for medical devices. This material (and others like it that can be used in Y-connector embodiments claimed herein) provides a strong inner core for Y-connector 100, including suitable small-bore connectors that meet appropriate standards, guidelines and/or other requirements (e.g., ISO 80369-1:2010 covering small-bore connectors for liquids and gases in healthcare applications). Also, because the rigid material in some Y-connector embodiments is clear, a user is able to confirm visually that connections have been made, to confirm visually that administration is occurring, and to determine visually the cleanliness of the Y-connector 100 before, during and/or after use. Core unit 110 also can be made of a translucent or opaque material, including materials that can possess preselected color characteristics. Core unit 110 can be a single, unitary plastic structure or can be constructed of several components, for example by adhesive or solvent bonding.

Over-layer 114 is made of a pliable material such as a thermoplastic elastomer in some embodiments. When such an elastomer is used, it can be a medical-compliant overmold that adheres to various substrates, including the types of rigid material used in core unit 110, noted above. This type of material has a rubber feel and soft touch and is clear or translucent; it also can be used in injection molding fabrication. Over-layer 114 also can be made of an opaque material, including materials that can possess preselected color characteristics. Over-layer 114 provides a good gripping material for individuals who are handling and manipulating the Y-connector 100 (e.g., nurse, clinician, caregiver, patient, etc.) and also provides a resilient enclosure that permits the use of a rigid material for core unit 110 while protecting core unit 110 from breakage, damage, slipperiness and other undesirable characteristics. Moreover, the soft, flexible material of over-layer 114 allows Y-connector 100 to be placed in close proximity to a patient's face or other exposed skin more comfortably. The combination of core unit 110 and over-layer 114 permits an organic, smooth shape that allows for ergonomic gripping of Y-connector 100 during use.

Embodiments of a dual material Y-connector herein comprise a primary arm and one or more secondary arms that provide fluid flow (i.e., gas flow and/or liquid flow) through the Y-connector. As seen in the detailed view of the core unit 110 in FIG. 11, the primary arm includes a generally cylindrical primary arm stem 122. A primary arm small-bore connector 124 is positioned at the outer end of primary arm stem 122. Primary arm stem 122 defines an interior primary arm channel 125. In some embodiments the primary arm stem 122 and its associated small-bore connector 124 are components of an integral core unit 110 (e.g., in the case of the entire core unit 110 being a single, unitary plastic structure). In other embodiments small-bore connector 124 can be affixed to stem 122 using adhesive, solvent bonding, radio-frequency (RF) welding and/or any other suitable means of affixing connector 124 to stem 122. Various aspects of the core unit 110 can be separately constructed and then affixed to one another in a similar manner in various embodiments.

Figure 11:
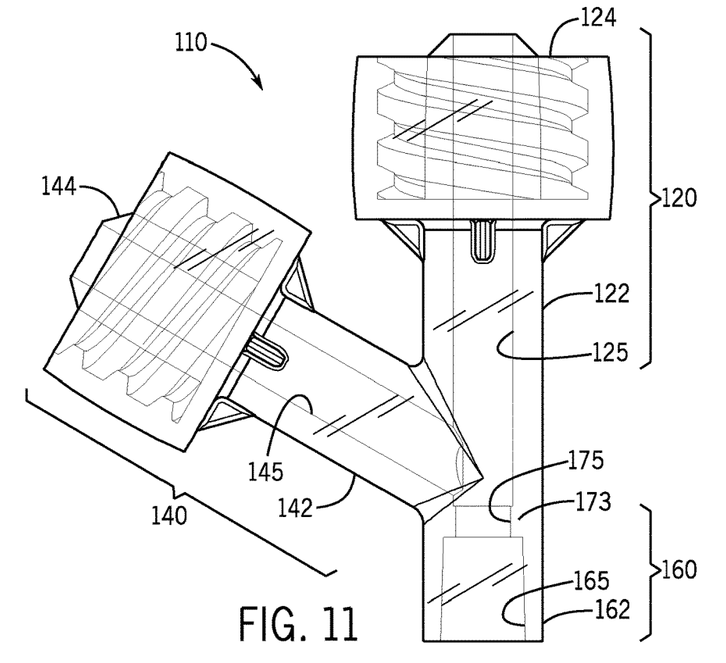
FIG. 11 is a side view of a dual material Y-connector inner core according to one or more embodiments.
Figure 12:
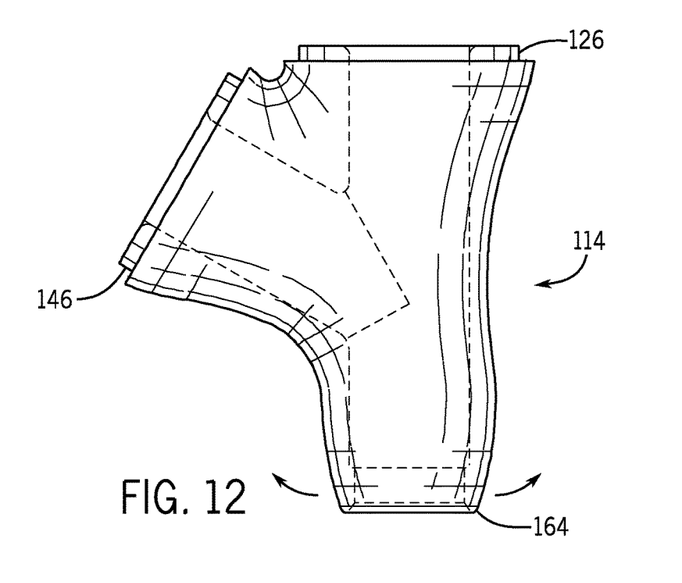
FIG. 12 is a side view of a dual material Y-connector over-layer according to one or more embodiments.

Similarly, the secondary arm includes a generally cylindrical secondary arm stem 142. A secondary arm small-bore connector 144 is positioned at the outer end of secondary arm stem 142. Additional secondary arms can be implemented in similar fashion. Secondary arm stem 142 defines an interior secondary arm channel 145. In some embodiments each secondary arm stem 142 and its associated small-bore connector 144 are components of an integral core unit 110. In other embodiments small-bore connector 144 can be affixed to stem 142 using adhesive, solvent bonding, radio-frequency (RF) welding and/or any other suitable means of affixing connector 144 to stem 142.

The convergence arm also includes a convergence arm stem 162 shown in FIG. 11. In some embodiments convergence arm stem 162 is a component of an integral core unit 110. In other embodiments stem 162 can be affixed to one or more components of core unit 110 using adhesive, solvent bonding, radio-frequency (RF) welding and/or any other suitable means.

Figure 7:
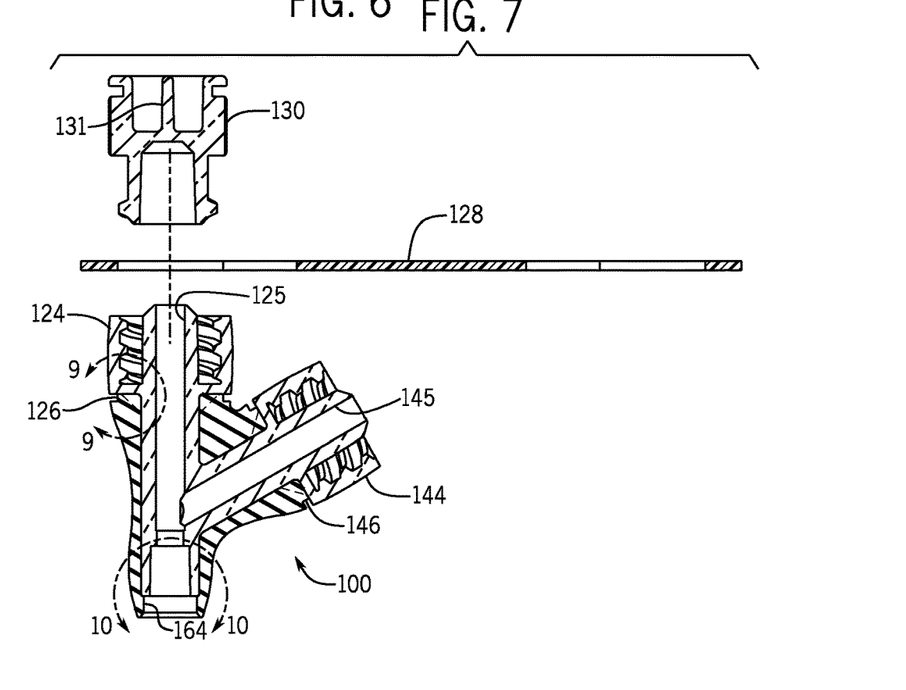
FIG. 7 is a cross-sectional view of a dual material Y-connector according to one or more embodiments.
Figures 8, 9, 10:
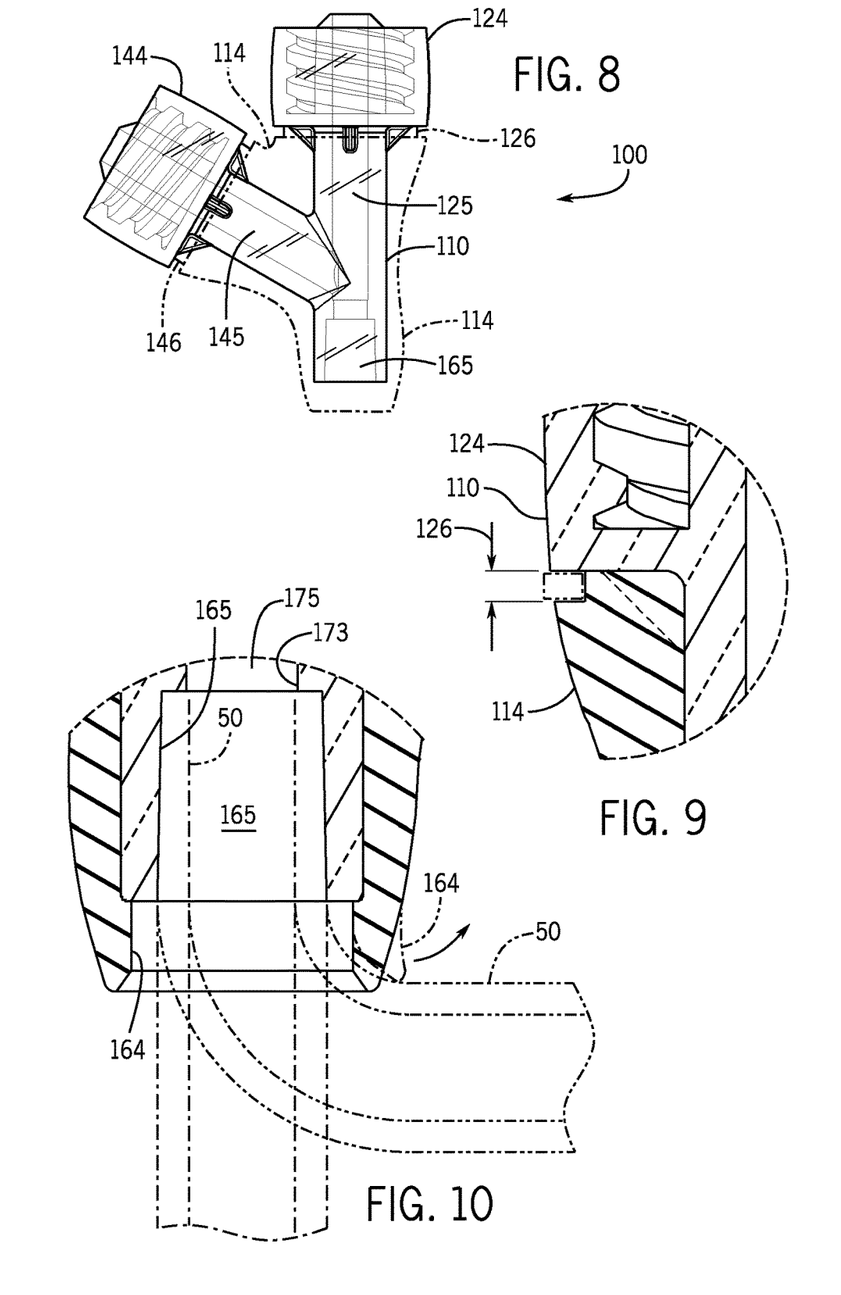
FIG. 8 is side view of a dual material Y-connector according to one or more embodiments in which an inner core unit is illustrated along with an over-layer shown in phantom.
FIG. 9 is a detailed cross-sectional view defined by the line 9-9 of FIG. 7.
FIG. 10 is a detailed cross-sectional view defined by the line 10-10 of FIG. 7.

FIGS. 7, 8 and 11 illustrate detailed information regarding one or more embodiments of the core unit 110. Primary arm 120 and convergence arm 160 are generally coaxial, providing a generally linear flow path (of varying diameters in some embodiments) for fluids flowing between (to and/or from) primary arm 120 and convergence arm 160. Secondary arm 140 is of similar construction to primary arm 120, but is oriented at an angle of approximately 60° relative to primary arm 120 and convergence arm 160 in the non-limiting exemplary embodiments of the Figures. Other angular orientations between primary and secondary arms 120, 140 are implementable as well. Generally, the likelihood of clogging or other improper flow problems increases as the angle of second feed arm 140 gets closer to 90°. In some uses performance may also be reduced or otherwise affected with changes in this angular orientation.

The inner bore diameter of interior channels 125, 145 of primary arm 120 and secondary arm 140, respectively, may be different than the inner bore diameter of convergence arm 160 in some embodiments. Interior channel diameters may be dependent upon the type of connection used between dual material Y-connector 100 and any tubing segment(s) transmitting fluid to or from the connector 100. As shown in FIGS. 10 and 11, an interior annular neck 173 in the interior of core unit 110 can define a linking channel 175 in some embodiments.

The interior annular neck 173 defining linking channel 175 can serve as an anchoring point for a tubing segment or similar attachments to the convergence arm 160. In some embodiments, as seen in FIG. 10 for example, tubing 50 can be solvent bonded to one or more interior surfaces of the core unit 110 (e.g., to the annular abutment of neck 173 and/or to the inner surface of interior channel 165). Other means of affixing tubing segment 50 to Y-connector 100 are well known.

The bores of arms 120, 140 typically are dictated by dimensions permitted within a given standard or other specific definition (e.g., ISO 80369-3), which can be defined for reducing misconnection potential. The bore size of convergence arm 160 important in relation to the size of tubing 50 that is attached to it. In some embodiments the smallest inner diameter of the convergence arm 160 is no smaller than the inner diameter of the attached tubing.

In some Y-connector embodiments usable with enteral feeding systems, for example, the interior channel 125 of primary arm 120 and the interior channel of secondary arm 140 each can have an interior bore of approximately 2.90 mm and the inner bore of interior channel 165 of convergence arm 160 can be approximately 3.86 mm. In some embodiments channels 125, 145 are connected to channel 165 using an even smaller diameter linking channel 175, as seen in FIGS. 7, 8 and 11. This linking channel 175 can have an inner bore of approximately 2.67 mm and a length of ~1.5 mm in some embodiments.

A portion of primary arm stem 122 is enclosed in the soft material of over-layer 114. As seen in FIGS. 8 and 9, a small circumferential gap 126 is provided between the primary arm small-bore connector 124 and the portion of over-layer 114 enclosing primary arm stem 122. Gap 126 allows a ring connector 128 or other suitable connector to be attached to primary arm 120 so that a small-bore connector cap 130 can be tethered or otherwise attached to primary arm 120. Gap 126 enables the ring connector 128 to swing or rotate circumferentially around small-bore connector 124, thus facilitating movement and positioning of connector 128 and cap 130 for better access by a clinician or patient to small-bore connector 124. Gap 126 also ensures that ring connector 128 remains connected to the Y-connector, thus preventing loss of cap 130 and allowing a nurse or other caregiver the ability to work with the Y-connector without the need of a tray, table or other work surface needed to hold Y-connector parts (e.g., while changing configurations).

As with primary arm stem 122, a portion of secondary arm stem 142 is enclosed by over-layer 114. A small circumferential gap 146 again is provided between the second feed arm portion of over-layer 114 and the secondary arm small-bore connector 144. Gap 146 allows a ring connector 148 or other suitable connector to be attached to secondary arm 140 so that a second small-bore connector cap 150 can be tethered or otherwise attached to secondary arm 140. Gap 146 enables the ring connector 148 to swing or rotate circumferentially around small-bore connector 144, thus facilitating movement and positioning of connector 148 and cap 150 for better access by a clinician or patient to small-bore connector 144. As with gap 126, cap 130 and ring connector 128, gap 146 also ensures that ring connector 148 remains with the Y-connector.

Caps 130, 150 are threaded covers that engage mating threads on small-bore connectors 124, 144, respectively. The configuration of each small-bore connector 124, 144 and its respective cap 130, 150 can conform to applicable national and/or international standards (e.g., ISO 80369-3 relative to connectors for enteral applications) for such connectors and the like.

The interior of caps 130, 150 can utilize whatever structure is effective to seal an inlet/outlet (e.g., one of the arms 120, 140) to prevent ingress of unwanted materials into and egress of internal materials from a system incorporating one or more Y-connectors 100 according to embodiments. The external configuration of each cap 130, 150 enhances ease of use for a nurse, clinician, etc. The cylindrical sidewalls on the periphery of each cap 130, 150 have gripping means 133 (e.g., knurling, grips, ridges or the like) to provide better gripping of the cap, especially if it is wet or has adhered material that makes disengagement from and/or securement to Y-connector 100 difficult.

Moreover, the circular top of each cap 130, 150 can have a double-D configuration 131, as seen in the Figures. This type of multi-indentation cap configuration, in which the top of the cap has multiple indentations, recesses, cavities or the like, allows a nurse, clinician, etc. to use a tool 195 (e.g., a cleat or pick) to assist in dislodging a stuck cap (e.g., if a cap was encrusted with material making cap disengagement difficult). Moreover, the multi-indentation cap configuration is advantageous from a fabrication perspective, for example by reducing mold processing challenges.

Over-layer 114 can be an over-mold shot as shown in FIGS. 7 and 8. In addition to providing the good gripping/handling characteristics and reinforcement noted above, the over-layer 114 also eliminates narrow joints where the secondary arm 140 meets the main body of Y-connector 100, instead providing a broader surface area that limits the amount of dirt that is allowed to accumulate and thus making Y-connector 100 easier to clean.

As noted above, the molding and/or structure of over-layer 114 leaves gaps 126, 146 for use of ring connectors or the like in some embodiments. Also, over-layer 114 does not enclose the small-bore connectors 124, 144 in some embodiments. However, over-layer 114 completely encloses convergence arm 160 and extends beyond the longitudinal end of convergence arm stem 162 in some embodiments. In addition to reinforcing the convergence arm component of the core unit 110, as seen in FIGS. 7 and 10, a pliable material extension 164 of over-layer 114 provides a pliable connection collar that functions as a stress relief extension for a tubing segment 50 or the like (e.g., in an enteral feeding system). As seen in FIG. 10, as tubing 50 is pulled sideways, stress relief extension 164 provides a yielding engagement (i.e., relief of lateral stress) between tubing 50 and Y-connector 100 to reduce the likelihood of kinking in or damage to tubing 50 that might slow or stop the flow of fluids (i.e., liquids and/or gases) through tubing 50.

The many features and advantages of the present invention are apparent from the written description, and thus, the appended claims are intended to cover all such features and advantages of the invention. Further, since numerous modifications and changes will readily occur to those skilled in the art, the present invention is not limited to the exact construction and operation as illustrated and described. Therefore, the described embodiments should be taken as illustrative and not restrictive, and the invention should not be limited to the details given herein but should be defined by the following claims and their full scope of equivalents, whether foreseeable or unforeseeable now or in the future.

The invention claimed is:

1. A Y-connector apparatus for use in connection with an enteral feeding system, the Y-connector apparatus comprising:
   a tubing segment;
   a Y-connector comprising an inner core made of a first material and an over-layer made of a second material, wherein the over-layer at least partially encloses the inner core;
   wherein the Y-connector comprises a primary arm, a secondary arm and a convergence arm all in fluid communication with one another;
   wherein the primary arm comprises a primary arm stem having a primary arm small-bore connector at an outer end of the primary arm stem, wherein the primary arm stem and primary arm small-bore connector are made of the first material;
   wherein the secondary arm comprises a secondary arm stem having a secondary arm small-bore connector at an outer end of the secondary arm stem, wherein the secondary arm stem and secondary arm small-bore connector are made of the first material;
   wherein the second material encloses at least a portion of the primary arm stem and at least a portion of the secondary arm stem;
   wherein the convergence arm comprises a convergence arm stem having an outer end and an interior channel, wherein the convergence arm stem is made of the first material;
   wherein the convergence arm stem is adapted to receive the tubing segment within the interior channel of the convergence arm stem;
   wherein the second material encloses the entire convergence arm stem; and
   wherein the over-layer is configured such that at least a portion of the tubing segment extends beyond the convergence arm and is not enclosed by the over-layer.

2. The Y-connector apparatus of claim 1, wherein the tubing segment is bonded within the interior channel of the convergence arm stem using one of the following: adhesive, solvent bonding, radio-frequency (RF) welding.

3. The Y-connector apparatus of claim 2 wherein the first material is a rigid plastic material.

4. The Y-connector apparatus of claim 3 wherein the second material is a pliable material.

5. The Y-connector apparatus of claim 4 wherein the first material is a transparent copolyester and further wherein the second material is a translucent thermoplastic elastomer.

6. The Y-connector apparatus of claim 1 further comprising a first cap configured to seal the primary arm and a second cap configured to seal the second arm.

7. The Y-connector apparatus of claim 6 wherein each cap comprises a top and a plurality of indentations in the top of the cap.

8. The Y-connector apparatus of claim 6 wherein each cap comprises gripping means.

9. The Y-connector apparatus of claim 6 wherein the first cap is coupled to the primary arm with a first tether configured to circumferentially rotate the first cap about the primary arm;
   further wherein the second cap is coupled to the secondary arm with a second tether configured to circumferentially rotate the second cap about the secondary arm.

10. The Y-connector apparatus of claim 9 wherein the first tether is coupled to the primary arm using a first circumferential gap between the inner core and the over-layer;
    further wherein the second tether is coupled to the secondary arm using a second circumferential gap between the inner core and the over-layer.

11. A Y-connector assembly comprising:
    a tubing segment;
    a hard plastic inner core comprising:
      a convergence arm comprising a convergence arm stem having an interior channel, wherein the convergence arm stem is adapted to receive the tubing segment within the interior channel of the convergence arm stem;
      a primary arm comprising a primary arm stem in fluid communication with the convergence arm stem; and
      a secondary arm comprising a secondary arm stem in fluid communication with the convergence arm stem and with the primary arm stem; and
    a pliable material over-layer enclosing at least a portion of the primary arm stem, enclosing at least a portion of the secondary arm stem, and enclosing at least a portion of the convergence arm stem, wherein the over-layer is configured such that at least a portion of the tubing segment extends beyond the convergence arm and is not enclosed by the over-layer;
    wherein the primary arm further comprises a primary arm small-bore connector at an outer end of the primary arm stem; and
    further wherein the secondary arm further comprises a secondary arm small-bore connector at an outer end of the secondary arm stem.

12. The Y-connector assembly of claim 11 wherein the hard plastic inner core is made of a transparent plastic material.

13. The Y-connector assembly of claim 11 wherein the pliable material over-layer encloses the entire convergence arm stem.

14. The Y-connector assembly of claim 13 further comprising an over-layer stress relief extension that extends beyond an outer end of the convergence arm stem.

15. The Y-connector assembly of claim 11 further comprising:
    a primary arm cap tethered to the primary arm and configured to seal the primary arm small-bore connector; and
    a secondary arm cap tethered to the secondary arm and configured to seal the secondary arm small-bore connector.

16. The Y-connector assembly of claim 15 wherein the primary arm cap is configured to engage threading in the primary arm stem small-bore connector; and further wherein the secondary arm cap is configured to engage threading in the secondary arm stem small-bore connector.

17. A Y-connector assembly comprising:
    a tubing segment;
    an inner core comprising a hard material and further comprising:
      a primary arm stem having a primary arm small-bore connector at one end of the primary arm stem;

a secondary arm stem having a secondary arm small-bore connector at one end of the secondary arm stem; and a convergence arm stem having an interior channel;

wherein the convergence arm stem is adapted to receive the tubing segment within the interior channel of the convergence arm stem;

wherein the primary arm stem, secondary arm stem and convergence arm stem are all in fluid communication with one another; and an over-layer enclosing at least a portion of the primary arm stem, at least a portion of the secondary arm stem, and at least a portion of the convergence arm stem, wherein the over-layer is comprised of a pliable material, and wherein the over-layer is configured such that at least a portion of the tubing segment extends beyond the convergence arm stem and is not enclosed by the over-layer.

18. The Y-connector assembly of claim 17 wherein the over-layer encloses the entire convergence arm stem and comprises a stress relief extension that extends beyond the convergence arm stem.

19. The Y-connector assembly of claim 17 wherein the primary arm further comprises a primary arm cap tethered to the primary arm and configured to seal the primary arm stem; and further wherein the secondary arm further comprises a secondary arm cap tethered to the secondary arm and configured to seal the secondary arm stem.

* * * * *